(12) United States Patent
Dharia

(10) Patent No.: US 7,059,198 B2
(45) Date of Patent: Jun. 13, 2006

(54) APPARATUS TO DETERMINE ABILITY OF PLASTIC MATERIAL TO BE SHAPED BY THERMOFORMING PROCESS

(75) Inventor: Amitkumar N. Dharia, 387 Graham Dr., Coppell, TX (US) 75019

(73) Assignee: Amitkumar N. Dharia, Coppell, TX (US)

( * ) Notice: Subject to any disclaimer, the term of this patent is extended or adjusted under 35 U.S.C. 154(b) by 60 days.

(21) Appl. No.: 10/920,127

(22) Filed: Aug. 17, 2004

(65) Prior Publication Data

US 2006/0037406 A1    Feb. 23, 2006

(51) Int. Cl.
*G01N 3/08* (2006.01)
(52) U.S. Cl. .......................................... 73/821
(58) Field of Classification Search ............... 73/818, 73/821, 824, 766
See application file for complete search history.

(56) References Cited

U.S. PATENT DOCUMENTS

| | | | |
|---|---|---|---|
| 3,671,624 A * | 6/1972 | Antalek et al. ............. 264/294 |
| 3,751,977 A | 8/1973 | Schilling | |
| 3,787,158 A * | 1/1974 | Brown et al. ............... 425/156 |
| 4,034,602 A | 7/1977 | Woo | |
| 4,297,884 A | 11/1981 | Leveque | |
| 4,541,270 A * | 9/1985 | Hanslik ...................... 73/54.11 |
| 4,674,972 A | 6/1987 | Wagner | |
| 4,692,111 A | 9/1987 | Wagner | |
| 4,882,930 A * | 11/1989 | Nagy et al. ................. 73/54.11 |
| 5,047,964 A * | 9/1991 | Lalli ........................... 702/130 |
| 5,262,101 A * | 11/1993 | Yagi et al. ................... 264/410 |
| 5,620,715 A * | 4/1997 | Hart et al. ................... 425/143 |
| 5,795,535 A | 8/1998 | Giovannone | |

OTHER PUBLICATIONS

Frank Esposito, Plastics News, "TTG to offer thermformer for testing" Jan. 6, 2003.

\* cited by examiner

*Primary Examiner*—Max Noori
(74) *Attorney, Agent, or Firm*—Amitkumar N. Dharia

(57) ABSTRACT

A device to evaluate the thermoformability of plastics using pressure, vacuum or both is provided. The device includes at least one set of adjustable radiant heater panels laid parallel to the plastic material, a non-contact temperature measuring device, a carriage to move the plastic heated to preset temperature to forming, where a forming die attached to an end of mechanical device moves downwards or upwards at an adjustable speed forcing the heated plastic material to conform to the outer shape of the die while providing the actual force required to push the hot plastic as function of time or forming distance. A processor under the control of software measures the thermoforming characteristics of the sample.

20 Claims, 4 Drawing Sheets

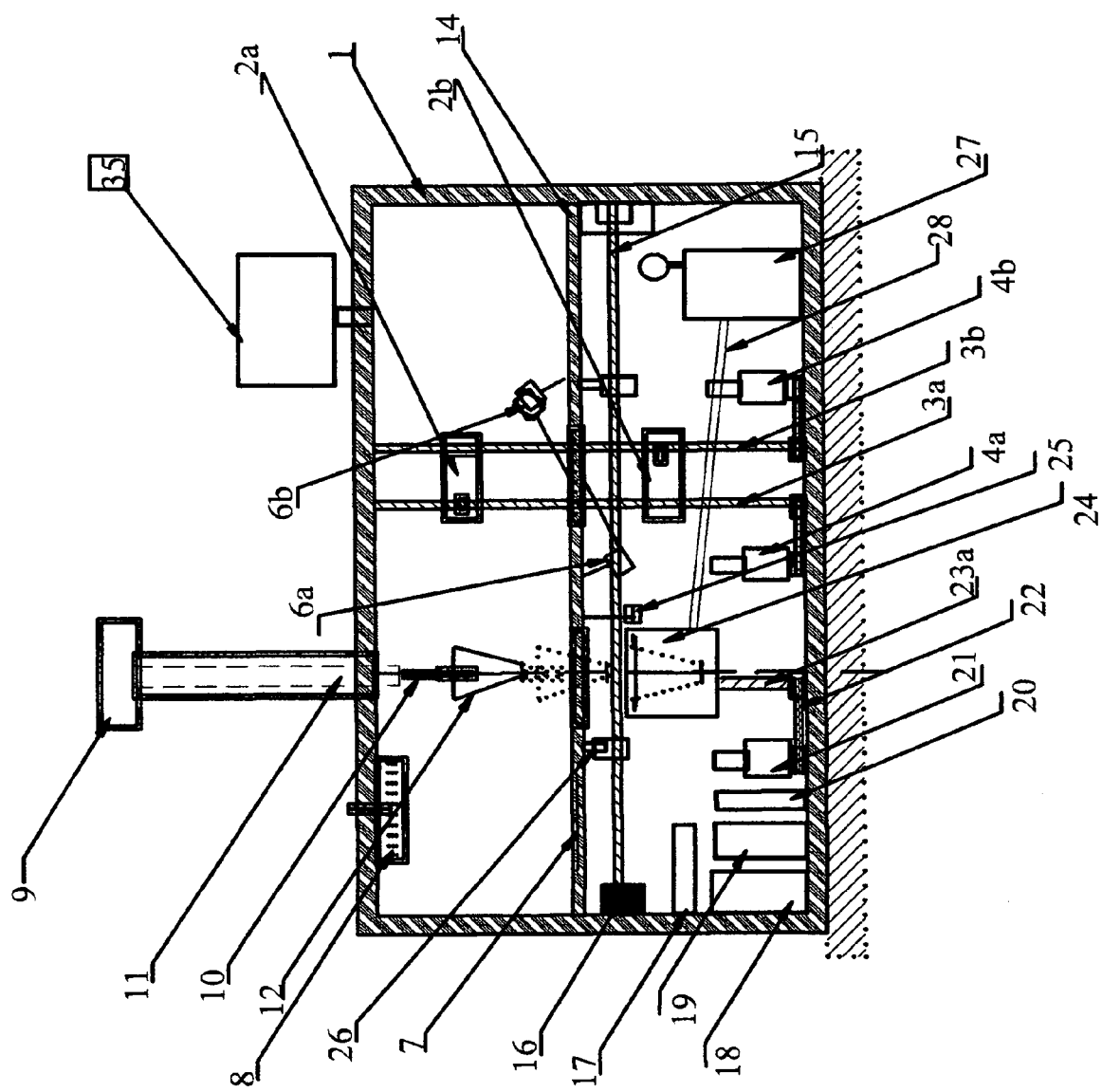
Figure-1 Back view

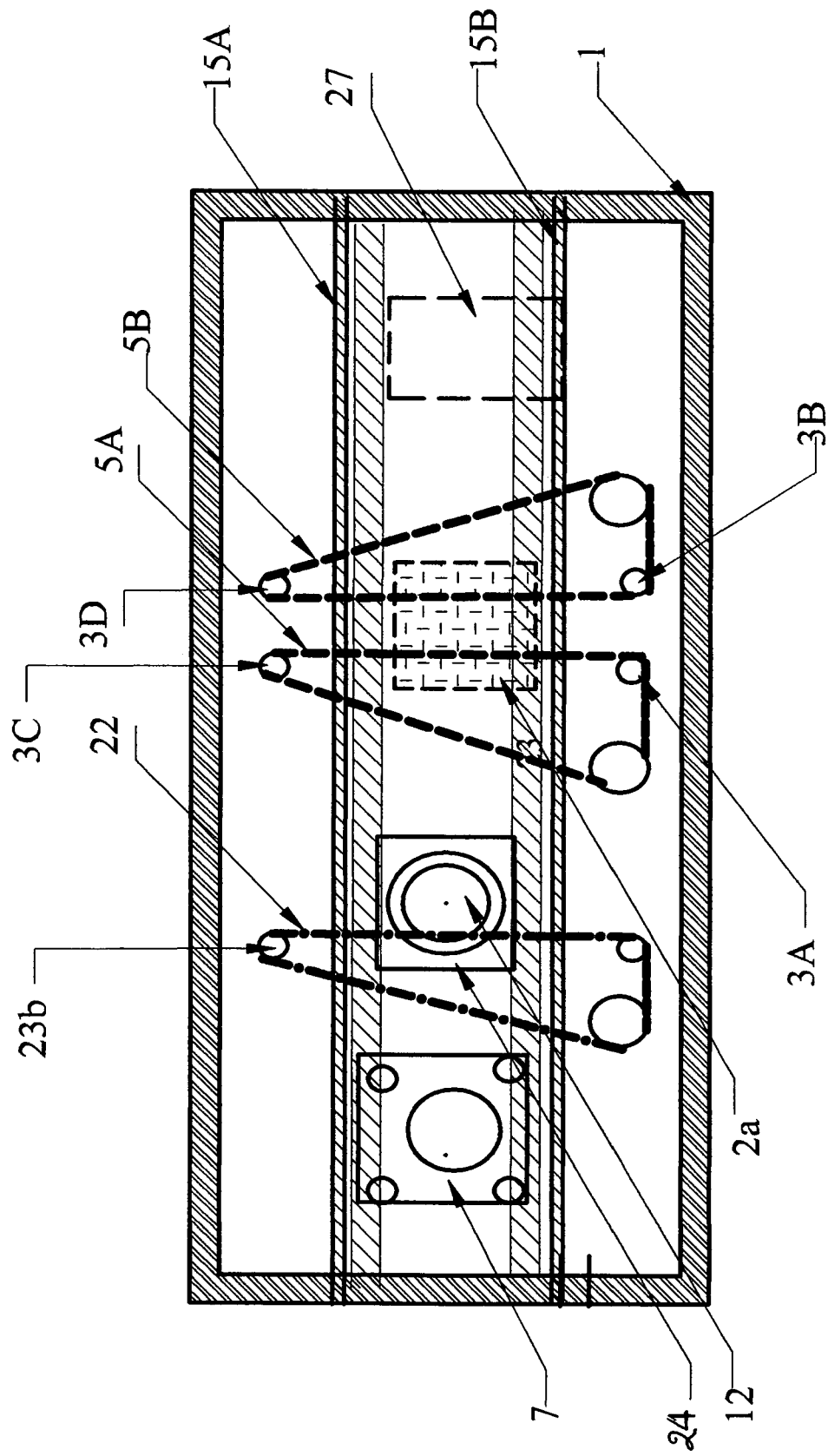
Figure-2 Top View (section A-A)

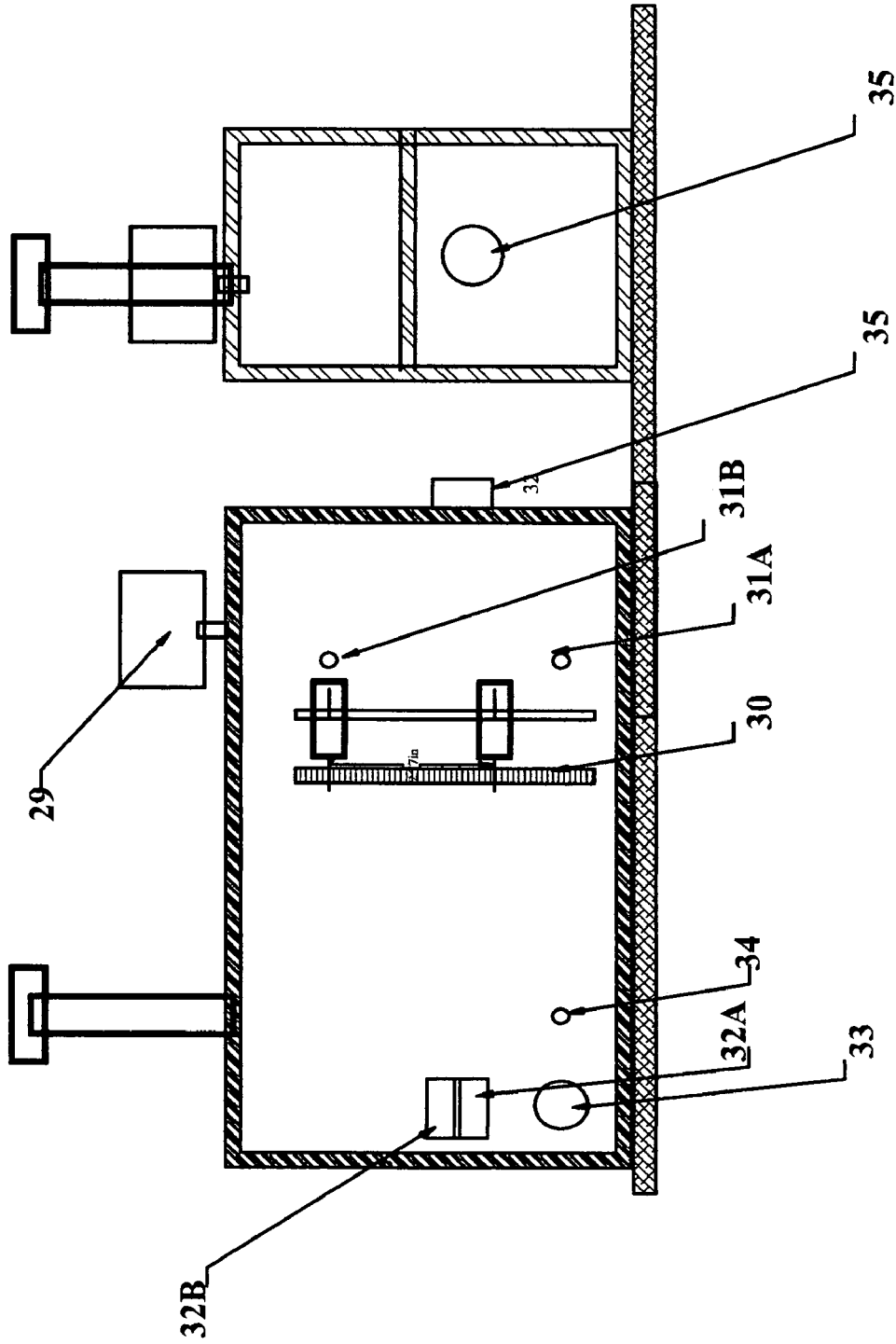

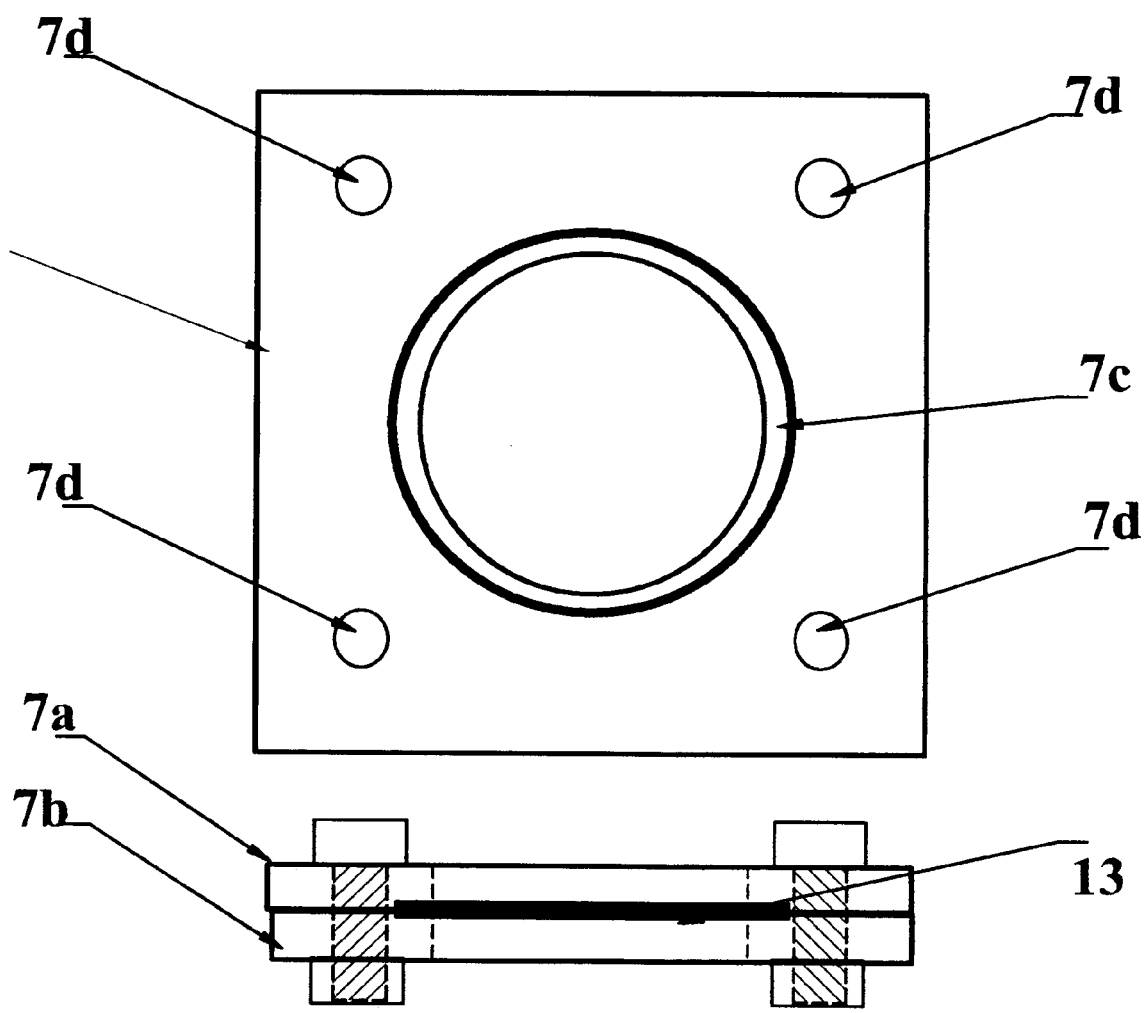
Figure-5 Sample Holding Tray

APPARATUS TO DETERMINE ABILITY OF PLASTIC MATERIAL TO BE SHAPED BY THERMOFORMING PROCESS

FIELD OF THE INVENTION

The present invention is directed to the field of thermoformed plastics. In particular, the invention is directed to a test apparatus which can determine and test the ability of a plastic to be thermoformed.

BACKGROUND OF THE INVENTION

The present invention relates to a novel apparatus to determine the ability of plastic material to be shaped by the thermoforming process using small amounts of material, under repeatable and controllable process conditions.

Parts and components, which range from those having very large surface areas to those having nominal thicknesses, are often shaped by the thermoforming process. The thermoforming process consists of (1) clamping a sheet of plastic, (2) heating the clamped sheet to plasticating temperature, (3) forming or shaping heated sheet using a suitable mold and counter mold system, (4) cooling a hot formed part, and (5) trimming the edges. In essence, thermoforming is a process of stretching heated sheet to conform to a desired shape either by pulling a stretched sheet over the female mold by applying a vacuum or by pushing heated sheet by a male mold moving downward as in positive forming or upwards as in negative pressure forming.

The ability of plastic material to be shaped by the thermoforming process depends on the rate of change in the strength or the elastic modulus of material with the change in temperature. Thus, highly crystalline materials such as polyamide, polyesters, and polypropylene having sharp melt transition, i.e. very high strength below melting point and very low strength above melting point, are difficult to thermoform, while amorphous materials such as rigid or plasticized PVC, PMMA, PS, ABS, SAN, SMA, which show gradual decrease in strength, with increase in temperature, can be thermoformed relatively easily.

The strength of a plastic material increases with its molecular weight. Hence, materials with a higher initial molecular weight will retain relatively higher strength upon heating than those materials with lower initial strength. The higher molecular weight materials with lower melt elasticity, or narrow molecular weight distribution, cannot be stretched or drawn to a higher level. The ability of a material to stretch also depends on the degree of entanglement. At equivalent molecular weight, molecules with low level of long chain branches such as LDPE tend to draw more than materials with relatively short branches, such as polypropylene. In addition to crystallinity, molecular weight, molecular weight distribution and the length of side chains, thermoformability will also vary with the orientation, amount and type of fillers, the amount and type of plasticizers, the amount and type of pigments, the amount of trim or recycled content, the thickness and weight variation, the degree of residual stresses along and across the extruded web, and sheet thickness. In addition, thermoforming also depends on the ability of material to uniformly absorb heat energy, sheet temperature, applied force, and the ability to resist degradation or embitterment upon heating.

Thus, for a plastic processor, it is very difficult to predict whether a newly developed material or slightly adjusted composition, new lot of extruded sheet stock made of same material, or sheet stock containing varying amount of recycled trim will thermoform well or not; or the proper process conditions the given material can be thermoformed to desired shape.

The actual field scale testing of thermoforming, even though most informative, is cost prohibitive. In many cases, large amounts of material required to make test sheet stock is not available, or equipment to make wide web required for commercial size machine may not be readily available, or enough sheet stock may not be available to adjust process parameters. In other situations, the processor may want to quickly establish starting process conditions for a given material without creating too much of start-up scrape, needs to sort out good lot from a bad lot, or make quick adjustments from virgin to recycled trim blend ratio.

One of the methods used to estimate thermoformability is hot tensile test, described in ASTM D 638, according to which injection molded or die-cut dog-bone shaped sample is stretched at uniform speed at forming temperature. Hot tensile tests are difficult to carry out with any degree of reliability or confidence in data. At forming temperature, uni-axial stretching is not confined to the neck-down portion of the sample. Grip-slip or extrusion of plastic from grips is common. Further, long conditioning time required to achieve desired temperature can induce annealing and stress relaxation, both affecting the measured tensile modulus.

Hot creep is another uni-axial test in which fixtured sample is placed in a heated oven without load, and after it reaches to equilibrium temperature, a very high load is applied instantaneously. High-speed video camera is used to determine time dependent elongation to break at that temperature. Although test is relatively simple, interpretation of the results is difficult. Even though hot creep test data suffers from the same vagaries of the hot-tensile test, hot creep test is more sensitive and provides cleared stress-strain data at high strain rate levels.

The stretchability of material in melt phase is also evaluated using a melt-tensiometer. In this test, a thin strand of material is extruded using a strand die and strand is stretched at uniform and controllable velocity using a pulling device equipped with force sensors. The amount of force required at various velocities is measured and draw velocity at which strand breaks is noted as maximum draw velocity. Even though this test is very useful in comparing melt strength of different materials, it does not reflect the real thermoforming process, which is carried out in semi-solid phase, and in which the material is stretched in all three directions.

Other stretching tests involve inflating a heated circular disk of test material at constant pressure and determining rate of biaxial stretching using high-speed video camera. The result is then used to determine appropriate constants in stress-strain equations. Such test can be used for relatively thin films only and test results are not directly applicable to thermoforming process.

Stress-strain behavior as function of time can be tested using a dynamic mechanical analyzer or DMA. DMA measures relative elastic modulus of material as function of temperature at fixed frequency of applying load or at fixed temperature as function of frequency. Even though DMA requires very small amount of material, and test results are highly accurate and repeatable, DMA is expensive and requires highly skilled personnel to operate and interpret data. Further, it does not reflect actual thermoforming process.

One of the most widely used tests is the sag resistance test. In this test, a rectangular or circular sample of sheet feed stock is clamped between two plates and placed in a heated oven. The time for sample to sag under its own weight by fixed distance or distance sagged for fixed time at given temperature is then determined. Even though easy and least expensive, results of sag tests are specific to geometry, i.e. size and shape of sample, and the size of sample changes during test. Further, most extruded sheet has residual stresses, which tends to relax upon heating it. This negative sag is not accounted for in a typical sag test.

Thus, among a variety of tests available, some are highly precise and repeatable, others are simpler but less precise and lack repeatability, and most of all none truly replicate the actual tri-axial stretching phenomenon taking place in thermoforming process.

The patent literature is replete with thermoforming-related inventions. U.S. Pat. No. 4,034,602 discloses an instrument for determining the complex mechanical response of samples incorporates two parallel sample arms each pivotally mounted at their central portion by flexure pivots of precisely known spring constants. The sample is mounted on one end of each. An electro-mechanical driver acts on the other end of one arm to maintain the arms and sample in mechanical oscillation about the pivots. A displacement transducer senses the mechanical motion. A feedback amplifier between the displacement transducer and the driver maintains the oscillation at a constant amplitude and at a resonant frequency determined primarily by the sample. With this arrangement the driver and displacement sensor are removed from the sample and its usual thermal chamber. This improves the stability of the instrument. At the same time the arms are dynamically balanced about the pivots and hence are relatively insensitive to vibrational upset.

U.S. Pat. No. 5,795,535 discloses a precut die apparatus arranged and adapted for use in a thermoform-trimming method and system to produce plastic molded articles, and to the method and system in which the apparatus is employed. The precut apparatus is positioned, in the method and system, between the form press and the trim station. The precut apparatus is arranged to precut, in a desired and selected manner, the thermoformed sheet material containing thermoformed articles therein, about the periphery of the thermoformed articles. The precut provides for a bridged and joining area of the sheet material to allow for slight movement and adjusting of the molded articles for precise alignment in the punch and die trim step of the thermoforming and trimming operation.

U.S. Pat. No. 4,692,111 discloses an apparatus for forming plastic articles by a thermoform process. A plastic sheet to be formed is die cut to a predetermined shape, heated, and draped over a male mold extending vertically upward. A vacuum is drawn internally of the male mold forming an imprint in the sheet from a die carried on the outer uppermost surface of the mold. A mating female mold is then lowered about the male mold to press the sheet about the conforms of the outer surface of the male mold until the plastic sets, thereby forming the desired object.

U.S. Pat. No. 4,674,972 discloses an apparatus for forming plastic articles by a thermoform process. A plastic sheet is supported between an upper female and lower male mold. The heater assembly is moved horizontally over the sheet, which is heated and caused to conform to the lower molds shape when the upper mold is lowered thereabouts, thus forming the desired object. Vacuum means retain the formed object within the upper mold assembly during separation of the molds and deposits the formed object on the top of the heater assembly upon its repositioning over the lower mold to heat a subsequent sheet. The formed object is carried away from the molds on the top of the heater assembly upon subsequent horizontal retraction of the heater assembly from between the molds. An air jet from an orifice on the top surface of the heater assembly then propels the formed object onto a conveyor belt.

U.S. Pat. No. 4,297,884 discloses a method of and apparatus for the measurement of at least one mechanical property of an elastic material. Young's modulus and/or the internal damping factor of an elastic material are obtained by subjecting an area of the material to a sustained vibration. The presence of the material being tested changes the resonance of a mechanical resonator and determination of the changed resonance peak enables the required elastic characteristics to be obtained. The sample may be subjected to varying tension during testing and can conveniently be vibrated by signals obtained from a variable frequency generator although, preferably, an electronic circuit for vibrating the resonator has a feedback loop to operate as an electro-mechanical auto-oscillator.

U.S. Pat. No. 3,751,977 discloses an analyzing structure for determining properties such as elastic shear modulus and mechanical hysteresis of a material. A pair of mutually spaced holders hold the sample in such a way that the holders are interconnected by the sample, and these holders are in turn carried by driver and driven supports. A drive sets the driver support into vibratory motion so that the latter is transmitted through the sample to the drive support. By detecting the manner in which the driver and driven supports vibrate it is possible to determine properties of the sample. The sample is tested by cyclically generating substantially pure shear forces in the sample, with the power required to sustain the vibrations of the sample at a constant level being measured to determine the damping of the sample and frequency of vibration being measured to determine the modulus of the sample.

While there are a number of patents directed to thermoforming technology, none are related to or disclose a technology for the testing of thermoplastic materials and for determining the propensity and ability of a material to be thermo-formed.

SUMMARY OF THE INVENTION

Accordingly, the principal object of the present invention is to provide a cut-sheet thermoformability analyzer, in which the effects of temperature, the amount of applied force, the speed of the applied force on the molded material, and the cooling time, can be measured and compared using a small amount of material without resorting to actual field trials.

Within the scope of the above-mentioned object, a further object of the invention is to provide an apparatus, which comprises a frame for easy and quick loading and unloading of samples.

Yet another object of the present invention is to provide an apparatus in which heat output of top and bottom heater panels can be independently adjusted, allowing more precise sheet surface temperature control.

Yet another object of the present invention is to provide an apparatus in which the distance between the sample surface and the top or bottom heater panel can be independently adjusted, allowing further control over top and bottom surface temperature.

Yet, another object of the present invention is to provide an apparatus in which the sample can be heated for a time period sufficient to achieve fixed surface temperature.

Yet a further object of the present invention is to provide an apparatus in which the sample surface temperature is measured and recorded as function of time, allowing determination of an upper process temperature limit for a given material.

Yet another object of the present invention is to provide an apparatus in which the plug velocity can be adjusted, allowing simulation of high and low strain rate process.

Yet another object of the present invention is to provide an apparatus in which the force required to form the part is measured and recorded as function of time or position of plug.

Yet another object of the present invention is to provide an apparatus in which part can be formed either by applying pressure or vacuum or both.

Yet another object of the present invention is to provide an apparatus in which heated sheet can be formed by a male plug moving downwards at controlled speed, as in positive pressure forming.

Yet, another object of the present invention is to provide an apparatus in which heated sheet can be formed by male plug moving upwards at controlled speed, as in negative pressure forming.

Yet another object of the present invention is to provide an apparatus in which heated sheet can be pre-stretched prior to forming.

Yet another object of the present invention is to provide and apparatus in which the distance by which sample being heated sags, can be monitored using a non-contact optical probe and displayed as well as recorded as function of temperature and time.

In one embodiment, the invention is a device to evaluate the thermoformability of test plastic test material using pressure, vacuum or both comprising: at least one heating member situated parallel to the plastic test material to heat the plastic test material, means for measuring the temperature of the plastic, a forming die moving at an adjustable speed to force the heated plastic material to conform to the outer shape of the die; and processor means for determining the force required to push the test material as a function of time and forming distance.

In a further embodiment, the invention is an apparatus to evaluate and calculate thermoforming criteria comprising: a carrier which moves a sample of thermoformable plastic sample to be tested from a loading station, heating station, forming station and back to unloading station; a heater unit for heating the thermoformable sample; a detachable mold which can be selectively moved in a direction at either a pre-determined force or at a pre-determined speed; a vacuum chamber with a mold underneath the forming station, which in vacuum forming or pre-stretching mode can be moved in a direction such as to mate with the surface of the sample; and processor means for determining and storing a calculation of the material being tested under formation.

In still a further embodiment, the invention is a system for testing a thermoformed piece of plastic comprising: a carriage for moving the plastic material sample to be tested between a first position and second position; a heater proximate to the second position for heating the plastic to a pre-selected temperature; a piston for compressing the plastic material; and processor means associated with the piston for determining a thermoforming property of the sample as the piston compresses the plastic sample.

In still a further embodiment, the invention is a system for testing thermo plastic comprising: a carriage for moving the plastic material sample to be tested between heater proximate to the second position for heating the plastic to a pre-selected temperature; and measuring means associated with a non-contact optical means for measuring distance by which sample being heated sags under its own weight.

In still a further embodiment, the invention is a method for testing a piece of plastic comprising the following steps: moving a sample tray carrying a plastic sample to a heating station; heating the plastic sample to a pre-programmed temperature such that it begins to sag under its own weight; measuring the distance of sag from it's original plane using a non-contact optical probe; storing data related to the distance of sag in a processor.

BRIEF DESCRIPTION OF THE FIGURES

FIG. 1 is a back view of the present invention.
FIG. 2 is a plan view of the present invention
FIG. 3 Front view of the present invention
FIG. 4 Right side view of the present invention
FIG. 5 Sample Holding tray

DETAILED DESCRIPTION OF THE PREFERRED EMBODIMENT

The present invention is described with reference to the enclosed figures wherein the same numbers are used. In particular, the present invention is directed to an apparatus for testing the properties of thermoformable materials and, in particular, properties that affect the temperature, the amount of force, strain rate, the speed of force, and the cooling ability.

The apparatus comprises a rectangular metal frame 1, with a carrier train 14 carrying a sample tray 7, extending the length of the apparatus, which may be moved by a pneumatic, hydraulic or programmable mechanical motor 16 by means of parallel lead screws 15A and 15B. The train moves a sample tray 7, which as shown in FIG. 5 comprises two rectangular sample holding plates, 7(*a*) and 7(*b*), comprising metal or heat resistant thermoset resin. The tray further includes a circular opening connected via spring loaded threaded fasteners 7(*d*), and having a rubber o-ring 7(*c*).

A rectangular piece of test material 13, either cut from web extruded using a small lab extruder equipped with a sheet forming die, or compression molded using lab hot press, is mounted in sample tray plates 7(*a*) and 7(*b*) and firmly held in position by tightening fasteners 7(*d*). The spring-loaded fasteners and thickness of gasket can be adjusted to accommodate thicker or thinner sheet while maintaining vacuum tight seal between sample and frame. The sample tray carrying a sample is placed on carrier train 14.

The tray loaded with sample is moved between two heaters 2(*a*) and 2(*b*). Heater 2(*a*) is connected to lead screws 3(*a*) and 3(*c*) which are attached to driving motor 4(*a*) by means of a driving belt 5(*a*), such that by means of switch 31 (*a*), can be moved to desired distance with respect to sample. Similarly, heater 2(*b*) is connected to lead screws 3(*b*) and 3(*d*) which are attached to driving motor 4(*b*) by means of a toothed driving belt 5(*b*), such that by means of switch 31(*b*) can be moved to desired distance with respect to sample. The distance of heater surface from sample surface is displayed on ruler means 30.

Further, by adjusting their respective controllers 32(*a*) or 32(*b*) temperatures of heater surface 2(*a*) and 2(*b*) is raised to desired degree by means of heater controllers 17. The top and bottom sample surface temperatures are measured by two non-contact pyrometers 6(*a*) and 6(*b*) and communicated to data processor 18. After either pre-programmed time or when sample surface reaches to pre-programmed surface temperature, sample tray is moved to forming station underneath the forming mold 12 connected to piston 11, which is driven by programmable servo-motor 9, making contact with limit switch 26(*a*), which in turn instructs servo-motor 9 to move piston 11 downward at pre-programmed speed. When the mold 12 makes contact with sample, force required to push sample is measured by a precision load cell 10 mounted between mold 12 and piston 11, and communicated to data processor 18.

After a pre-adjusted downward travel time, the piston will stay in position for an adjustable but pre-programmed time. At the end of the pre-set time, piston and plug will move upward, and sample tray is moved to initial loading station activating cooling fan 8 equipped with a programmable timer. The part will be cooled for adjustable but pre-programmed time. At the end of pre-set time, cooled part is manually removed from sample tray. A data processor under a computer program captures and stores the force, displacement, velocity, and temperature data during forming process.

In a second embodiment, the equipment provides for the shaping of heated sheet using the vacuum. In this mode, heated sample in a sample carrying tray moves to forming station underneath the mold 12, motor 21 connected to pinion 23(*a*) and 23(*b*) via driving belt 22, which in turn lift the vacuum chamber 24 made of perforated metal such as to make vacuum tight contact with sample tray 7(*b*). When a firm contact is established, limit switch 25 will be turned-on activating vacuum pump 27 which begins to draw air out of chamber 24 via connecting hose 28 allowing heated sheet to conform to inner surface of vacuum chamber 24. The change in air pressure during vacuum forming is communicated to processor. After pre-set time, vacuum will be released, vacuum chamber will lowered down, and sample tray will move to starting point for unloading formed sample.

In a third embodiment, the apparatus allows for the pre-stretching of heated sheet prior to forming. When heated sample tray moves underneath the forming piston, makes contact with limit switch 26, motor 21 is activated lifting vacuum chamber 24 by means of pinions 23 and driving belt 22. When vacuum chamber 24 makes firm contact with sample tray 7(*b*), limit switch 25 is turned-on which activates vacuum pump 27. The exhaust of vacuum pump carrying compressed air is forced through vacuum chamber such that the pre-heated film is stretched. After a pre-set stretch time vacuum pump turns off, the pressure plug 12 descends at pre-set speed shaping stretched sheet in to mold shape. Force value is measured, communicated to data processor and stored.

In yet another embodiment, the positions of male plug 12 and the vacuum chamber holding female cavity are reversed. When heated sample tray moves over the forming piston and makes contact with limit switch 26, motor 21 is activated, instructing vacuum chamber 24 to move downward and to make firm contact with top sample tray 7(*a*). When vacuum chamber hits limit switch 25, vacuum pump 27 begins to draw the air, thus forming part applying negative pressure.

In one embodiment, a sample tray 7 carrying sample is moved to heating station, where it is heated to pre-programmed temperatures, and as it begins to sag downward under its own weight, the distance from it's original plane is measured by means of a non-contact optical probe 35 and is communicated to processor 18 and displayed on display 35.

In beginning of each operation an operator is instructed to input selected mode of test operation, i.e. pressure forming, vacuum forming, sag resistance test, or negative forming along with the desired pre-heat time or surface temperature, speed of male plug, cooling time by means of computer software interfaced with heating elements, limiting switched, temperature controllers, all electric motors, load cell, non-contact optical and temperature probes, and cooling fan. In each mode of operation, the data processor controls the speed required to shape the material and the forming temperature, and stores force required to form. Such data can be used as received or can be further used as input in visco-elastic models to derive certain material parameters via mathematical processes. For further qualitative analysis. One can cut the part and check for draw depth at given temperature, thickness distribution, gloss variation, and shrinkage using secondary test methods.

From the above disclosure it should be apparent that the apparatus of present invention allows evaluating of material to be shaped by thermoforming process under precisely controlled condition and under various commercially adoptable forming modes, while using least amount of material. Further, apparatus allows controlling top and bottom surface temperature, most desired in forming thick or co-extruded sheet with base bonded to cap layer. Further, force vs. displace data at various speeds can simulate actual thermoforming process.

While the apparatus has been disclosed and illustrated with preferred embodiments thereof, it should be apparent that the disclosed embodiment is susceptible to several modifications and variations which will come within the spirit and scope of the invention.

I claim:

1. An apparatus to evaluate and calculate thermoforming criteria comprising:
   a carrier which moves a sample of thermoformable plastic from a loading position, heating position, forming position and back to loading position;
   a heater unit for heating the thermoformable sample;
   a detachable mold which can be selectively moved in a direction at either a pre-determined force or at a pre-determined speed;
   a vacuum chamber with a female mold underneath the forming position, which in vacuum forming or pre-stretching mode can be moved in a direction such as to mate with the surface of the sample; and
   processor means for determining and storing a calculation of the material being tested under formation.

2. The apparatus of claim 1 wherein the calculation comprises the effect of temperature of the sample.

3. The apparatus of claim 1 wherein the calculation comprises the speed of applied force.

4. The apparatus of claim 1 wherein the calculation comprises the quantity of force required to form the plastic.

5. A method for testing a thermoformed piece of plastic comprising the following steps:
   moving a sample tray carrying a plastic sample to a heating position;
   heating the plastic sample to a pre-programmed temperature such that it begins to sag under its own weight; and
   measuring the distance of sag from its original plane using a non-contact optical probe.

6. A device to evaluate the thermoformability or sag resistance of a plastic material in form of a single cut sheet using pressure, vacuum or both comprising:
   a framed enclosure comprising loading position, forming position, and a heating position;
   means for carrying the sheet sample;

means for moving the carrying means from the loading position to the heating position to the forming position and back to the loading position at a pre-selected constant speed;

two heating members situated on one side of the said forming station, one each on opposite sides of the sheet sample with the heating member oriented generally parallel to outer surfaces of the sheet to heat the plastic sheet on both sides for the same duration without contacting it;

means for continuously measuring and recording temperatures on both sides of the plastic sheet;

a forming die moving at a constant pre-selected speed to deform the heated sheet to conform to the outer shape of the die; and processor means for continuously measuring and storing the resistance of the heated sample to deformation as the forming die moves at the constant pre-selected speed as a function of distance.

7. The apparatus of claim 6 wherein the means for carrying the plastic sheet comprises two plates each having a center opening, and between which the sheet sample is positioned such that it completely covers the opening, wherein the sheet sample can be mounted freely on the carrying means for moving it to and from the loading, heating and forming positions.

8. The apparatus of claim 6 wherein the means for moving the sheet sample comprises a train which moves at the constant pre-selected speed in a single horizontal plain.

9. The apparatus of claim 6 wherein the forming position is at the same location as the loading position such that the loading, forming and unloading of the sample sheet is carried out at the same position.

10. The apparatus of claim 9 wherein the means for moving the sample sheet provides rotation in a single horizontal plain.

11. The apparatus of claim 6 which further comprises means for vertically moving the heating members to control their heat output independently of each other such that the two sides of the sample sheet can be heated at a constant rate to a specific pre-selected temperature or for a pre-selected duration.

12. The apparatus of claim 6 wherein the means for measuring the temperature of the sheet sample is not in contact with the outer surfaces of the sample sheet.

13. The apparatus of claim 6 which further comprises means for controlling the surface temperature of the forming die to a pre-selected value.

14. The apparatus to claim 6 wherein the constant speed of the forming die is up to 1000 mm/second.

15. The apparatus of claim 6 which further comprises a plug for assisting in deforming the sheet into the die, and means for changing the speed of movement of the plug at different points of the pre-selected forming distance.

16. The apparatus of claim 6 which further comprises controlling temperature inside the enclosure to the pre-selected temperature.

17. The apparatus of claim 6 which further comprises means for cooling the sheet sample after forming.

18. The apparatus of claim 1 wherein the calculation comprises the difference in force required to form the sample sheet at the pre-selected temperature and pre-selected speed to two different forming depths.

19. The apparatus of claim 1 which further comprises an ultrasonic sensor for continuously measuring the position of the sample sheet and means for recording such measurements.

20. A system for testing a ability of plastic to be shaped by thermoforming comprising:

a carriage for moving a plastic material sample to be tested between a first position and second position in a linear plane;

a heater proximate to the second position for heating the plastic to a pre-selected temperature;

a piston carrying a detachable die on its free end for forming the plastic material;

means to move piston at a constant speed to enable the die to contact and compress the heated plastic material; and processor means associated with the piston for determining a thermoforming property of the sample as the piston and die compresses the plastic sample.

* * * * *